(12) United States Patent
Litwin et al.

(10) Patent No.: US 6,635,063 B1
(45) Date of Patent: Oct. 21, 2003

(54) SET OF SURGICAL TOOLS AND SURGICAL METHOD FOR ANTERIOR CRUCIATE LIGAMENT RECONSTRUCTION

(75) Inventors: Yoram Litwin, Petach Tikva (IL); Ran Oren, Kibbutz Gaaton (IL)

(73) Assignee: T.A.G. Medical Products, Kibbutz Gaaton (IL)

( * ) Notice: Subject to any disclaimer, the term of this patent is extended or adjusted under 35 U.S.C. 154(b) by 0 days.

(21) Appl. No.: 09/241,428

(22) Filed: Feb. 2, 1999

(51) Int. Cl.[7] .............................. A61B 17/88
(52) U.S. Cl. .................... 606/104; 606/73; 606/232
(58) Field of Search .......................... 606/60, 72, 73, 606/86, 88, 104, 232; 623/13

(56) References Cited

U.S. PATENT DOCUMENTS

| | | | | |
|---|---|---|---|---|
| 5,207,679 A | * | 5/1993 | Li ................................ | 606/72 |
| 5,258,016 A | * | 11/1993 | DiPoto et al. ................ | 606/232 |
| 5,370,662 A | * | 12/1994 | Stone et al. .................. | 606/232 |
| 5,643,320 A | * | 7/1997 | Lower et al. ................. | 606/232 |
| 5,968,045 A | | 10/1999 | Frazier ......................... | 606/73 |

* cited by examiner

*Primary Examiner*—Michael Buiz
*Assistant Examiner*—David O. Reip

(57) ABSTRACT

A surgical inserter is provided which includes (a) a head portion formed with a ring acceptor for accepting a ring of the surgical screw; and (b) a neck portion connected to, or integrally formed with, the head portion. The neck portion is formed with two longitudinal grooves for engaging a folded band of connective tissue therein.

12 Claims, 4 Drawing Sheets

A-A

B-B

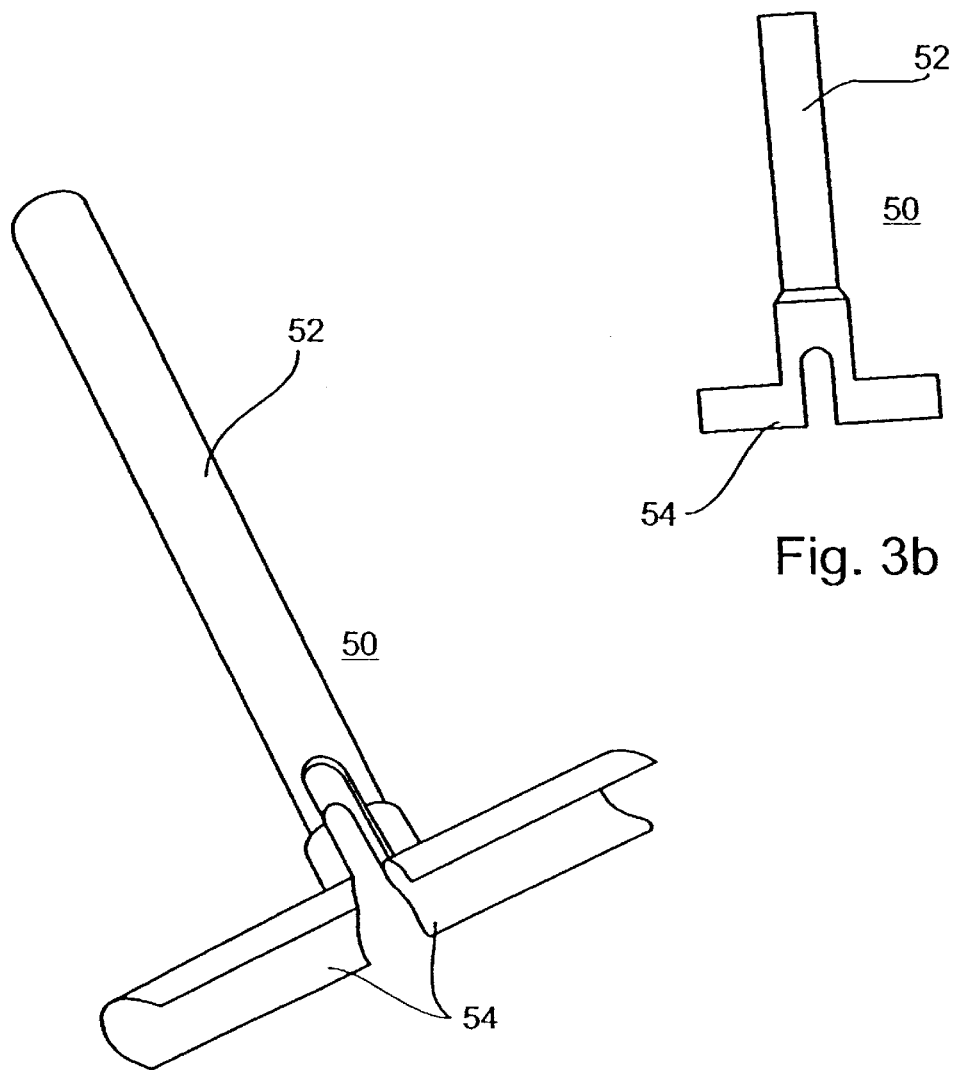
Fig. 3b
Fig. 3a
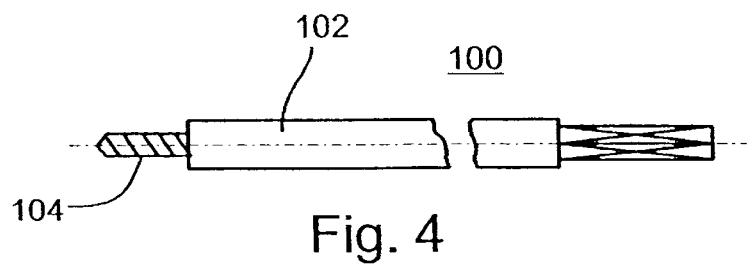
Fig. 4

SET OF SURGICAL TOOLS AND SURGICAL METHOD FOR ANTERIOR CRUCIATE LIGAMENT RECONSTRUCTION

FIELD AND BACKGROUND OF THE INVENTION

The present invention relates to surgical tools and method and, more particularly, to a set of surgical tools and a surgical method for anterior cruciate ligament reconstruction.

In certain instances following a knee injury, the anterior cruciate ligament which connects the femur and the tibia breaks and needs reconstruction.

The prior art teaches two main alternatives for anterior cruciate ligament reconstruction.

According to the first alternative, the medial part of the patella tendon, which connects the patella and the tibia, is used to reconstruct the anterior cruciate ligament. To this end, the medial part of the patella tendon is surgically removed along with bone portions of the patella and the tibia, which remain connected to the ends of the removed tendon portion. A first drill having an entrance opening and an exit opening is formed in the knee portion of the tibia and a co-aligned second drill having an entrance opening and a rear wall is formed in the femur, wherein the axis of the co-aligned drills is located substantially along the original path of the anterior cruciate ligament. The patella derived bone portion is inserted into the drill formed in the femur, whereas the tibia derived bone portion is inserted into the drill formed in the tibia, such that the medial part of the patella tendon is located substantially along the original path of the anterior cruciate ligament. Both bone portions are then fixated in place using interference screws.

The advantage of this procedure is that it allows immediate post operation full weight bearing. Its disadvantages include complications associated with the fact that portions of the patella and the patella tendon are removed, leading in some cases to fractures in the patella and/or tearing of the remaining portions of the patella tendon.

According to the second alternative, the semitendinosus or the semitendinosus and the gracilis of the pes anserinus tendon, which connects the tibia with the thigh muscle, are used to reconstruct the anterior cruciate ligament. To this end, the semitendinosus or the semitendinosus and the gracilis of the pes anserinus tendon are surgically removed. A first drill having an entrance opening and an exit opening is formed in the knee portion of the tibia and a coaligned drill also having an entrance opening and an exit opening is formed in the femur, wherein the axis of the co-aligned drills is located substantially along the original path of the anterior cruciate ligament. The semitendinosus or the semitendinosus and the gracilis of the pes anserinus tendon are folded to have a folded end and two free ends and are thereafter inserted into the drills formed in the tibia and the femur, such that the folded end of the semitendinosus or the semitendinosus and the gracilis of the pes anserinus tendon protrudes out of the exit opening of the drill formed in the femur, whereas the free ends of the semitendinosus or the semitendinosus and the gracilis of the pes anserinus tendon protrude out of the entrance opening of the drill formed in the tibia. Then, a surgical endobutton is attached to the folded end of the semitendinosus or the semitendinosus and the gracilis of the pes anserinus tendon via a suture, whereas the free ends of the semitendinosus or the semitendinosus and the gracilis of the pes anserinus tendon are attached to the tibial surface using surgical staples.

The advantage of this procedure is the avoidance of the complications associated with the alternative procedure. Its disadvantages include the formation of two, as opposed to one, drills having both entrance and exit openings, which increase the chances for post operation infections and further that full weight bearing can be exercised only about three weeks post operation.

There is thus a widely recognized need for, and it would be highly advantageous to have, a set of surgical tools and a surgical method which enjoy the advantages of the prior art procedures, yet devoid the limitations associated therewith.

SUMMARY OF THE INVENTION

According to one aspect of the present invention there is provided a surgical inserter for inserting through a drill formed in a bone and for screwing into a rear wall of the drill formed in the bone a surgical screw having a ring, through which ring a band of connective tissue being inserted, the surgical inserter comprising (a) a head portion being formed with a ring acceptor for accepting the ring of the surgical screw; and (b) a neck portion being connected to, or integrally formed with, the head portion, the neck portion being formed with two longitudinal grooves for is engaging the band of connective tissue therein, so as to enable inserting the surgical screw and the band of connective tissue through the drill formed in the bone, and screwing the surgical screw into the rear wall of the drill formed in the bone with minimized damage to the band of connective According to another aspect of the present invention there is provided a set of surgical tools comprising (a) a surgical inserter for inserting through a drill formed in a bone and for screwing into a rear wall of the drill formed in the bone a surgical screw having a ring, through which ring a band of connective tissue being inserted, the surgical inserter including (i) a head portion being formed with a ring acceptor for accepting the ring of the surgical screw; and (ii) a neck portion being connected to, or integrally formed with, the head portion, the neck portion being formed with two longitudinal grooves for engaging the band of connective tissue therein, so as to enable inserting the surgical screw and the band of connective tissue through the drill formed in the bone, and screwing the surgical screw into the rear wall of the drill formed in the bone with minimized damage to the band of connective tissue; and (b) a surgical sleeve for covering the inserter and the band of connective tissue while inserting the surgical screw and the band of connective tissue through the drill formed in the bone, and screwing the surgical screw into the rear wall of the drill formed in the bone.

According to yet another aspect of the present invention there is provided a surgical method of anchoring a band of connective tissue to a rear wall of a drill formed in a bone, the method comprising the steps of (a) providing a surgical screw having a ring; (b) inserting the band of connective tissue through the ring; and (c) using a surgical inserter, inserting the screw into the drill and screwing the screw into the rear wall of the drill.

According to still another aspect of the present invention there is provided an anterior cruciate ligament reconstruction surgical procedure comprising the steps of (a) forming a first drill in a tibia, the first drill having a first entrance opening and an exit opening, the exit opening facing a femur; (b) forming a second drill in the femur, the second drill having a second entrance opening and a rear wall of femur bone; (c) providing a surgical screw having a ring; (d) inserting a band of connective tissue through the ring; and (e) using a surgical inserter, inserting the surgical screw through the first drill into the second drill and screwing the screw into the rear wall of the second drill.

According to further features in preferred embodiments of the invention described below, the surgical method or procedure further comprising the step of covering the surgical inserter with a surgical sleeve, thereby protecting the band of connective tissue while inserting the screw into the drill and further while screwing the screw into the rear wall of the drill.

According to still further features in the described preferred embodiments the surgical inserter includes a head portion being formed with a ring acceptor for accepting the ring of the surgical screw and a neck portion being connected to, or integrally formed with, the head portion, the neck portion being formed with two longitudinal grooves for engaging the band of connective tissue therein.

According to still further features in the described preferred embodiments the surgical inserter further includes a handle connected to, or integrally formed with, the neck portion.

According to still further features in the described preferred embodiments the handle is removable.

According to still further features in the described preferred embodiments the ring acceptor is U-shaped.

According to still further features in the described preferred embodiments the ring acceptor includes undercuts formed in the head portion.

According to still further features in the described preferred embodiments the neck is round in cross section, whereas the two longitudinal grooves interfere with the roundness.

According to still further features in the described preferred embodiments the band of connective tissue is a band of an artificial connective tissue.

According to still further features in the described preferred embodiments the band of connective tissue is a band of a ligament, a tendon or a portion thereof.

According to still further features in the described preferred embodiments the band of connective tissue is derived from a pes anserinus tendon.

The present invention successfully addresses the shortcomings of the presently known configurations by providing surgical tools and a surgical method for anterior cruciate ligament reconstruction which enjoys low rates of post operation infections and complications and which allows immediate post operation full weight bearing. Thus, the present invention combines all of the advantages of the prior art procedures of cruciate ligament reconstruction described in the Background section above, while at the same time, avoids the limitations associated therewith.

BRIEF DESCRIPTION OF THE DRAWINGS

The invention herein described, by way of example only, with reference to the accompanying drawings, wherein:

FIGS. 3a–b are perceptive and side views of a surgical sleeve according to the present invention;

FIG. 4 is a side view of a drilling device according to the present invention.

DESCRIPTION OF THE PREFERRED EMBODIMENTS

Figure 1:
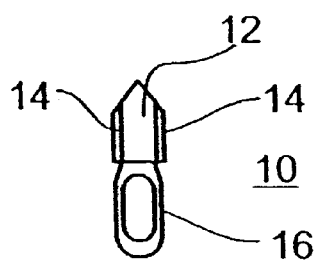
FIG. 1 is a side view of a surgical screw according to the present invention.

The present invention is of surgical tools and method which can be used to connect a band of connective tissue to a rear wall of a drill formed in a bone. Specifically, the present invention can be used to perform an anterior cruciate ligament reconstruction surgical procedure which enjoys low rates of post operation infections and complications and which allows immediate post operation full weight bearing.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates a surgical screw according to the present invention, which is referred to hereinbelow as surgical screw 10. Surgical screw 10 includes a screw head 12. The construction of screw head 12 is selected so as to enable screwing surgical screw 10 into a bone and further so as to permanently anchor surgical screw 10 in the bone. Thus, screw head 12 is preferably pointed and is preferably supplemented with thread 14. Surgical screw 10 further includes a ring 16. Ring 16 is connected to, connectable to (e.g., snappable to), or integrally formed with, screw head 12. Ring 16 serves for accepting a band of connective tissue therein, as further shown in FIG. 5.

Figure 2A:
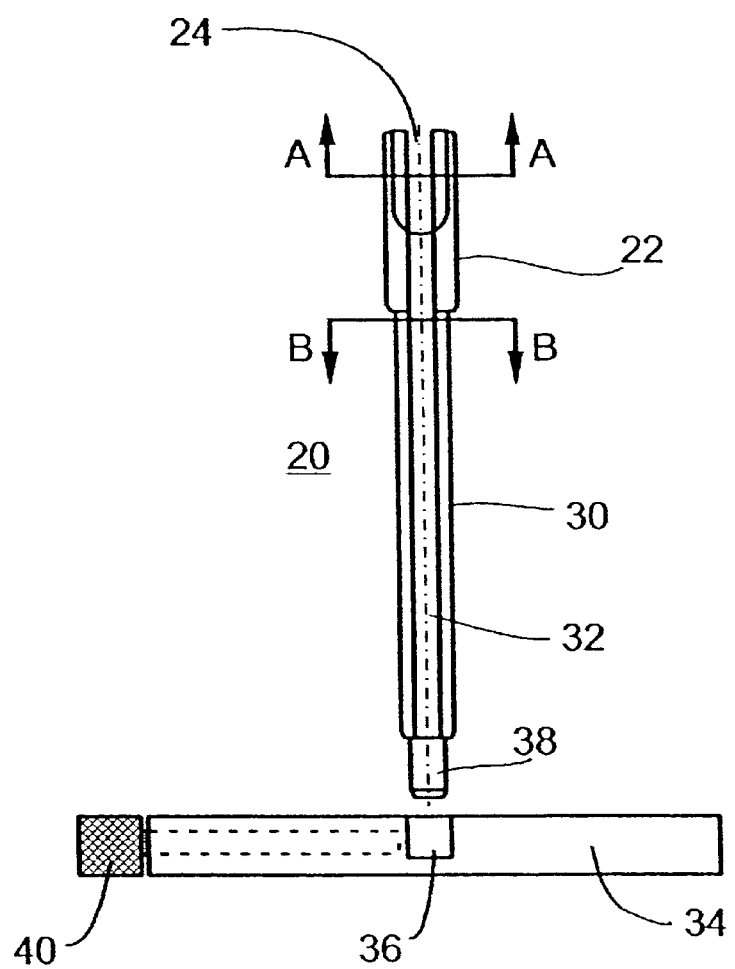
FIG. 2a is a side view of a surgical inserter according to the present invention.
Figure 2B:
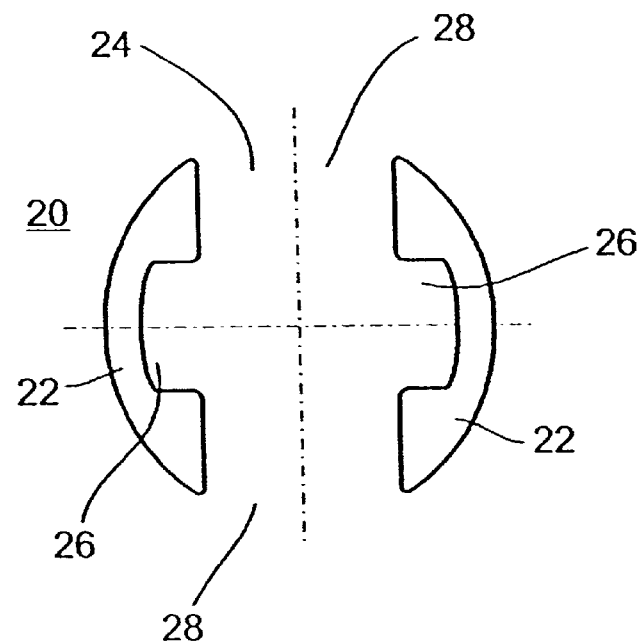
FIGS. 2b–c are cross sectional views of the surgical inserter of FIG. 2a along lines A—A and B—B, respectively.
Figure 2C:
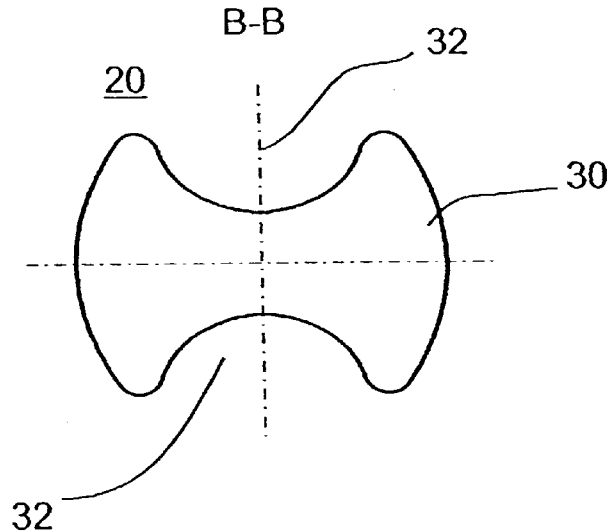

FIGS. 2a–c illustrate a surgical inserter according to the present invention, which is referred to hereinbelow as surgical inserter 20. Surgical inserter 20 serves, according to the present invention, to insert surgical screw 10 through a drill formed in a bone and to screw surgical screw 10 into a rear wall of the drill.

To this end, surgical inserter 20 includes a head portion 22 formed with a ring acceptor 24. Ring acceptor 24 serves for accepting ring 16 of surgical screw 10. The construction of ring acceptor 24 is selected so as to prevent swiveling of ring 16 therein. As best seen in FIG. 2a, ring acceptor 24 is preferably U-shaped and, as best seen in FIG. 2b, is formed to include undercuts 26 for accommodating and preventing the swiveling of ring 16 when engaged therein. Acceptor 24 is preferably formed with side openings 28 for allowing the band of connective tissue, which is inserted through ring 16, to hang out of head portion 22.

Surgical inserter 20 further includes a neck portion 30. Neck portion 30 is connected to, or integrally formed with, head portion 22. As further detailed hereinunder, the construction of surgical inserter 20 is selected so as to minimize the level to which the band of connective tissue protrudes from the general contour of inserter 20, so as to enable inserting surgical screw 10 and the band of connective tissue engaged therewith via ring 16 through the drill formed in the bone, and screwing surgical screw 10 into the rear wall of the drill formed in the bone while ensuring that minimal damage is imposed on the band of connective tissue. To this end, neck portion 30 of inserter 20 is formed with two longitudinal grooves 32. Grooves 32 serve for accommodating the band of connective tissue in a fashion that reduces the friction thereof with the side walls of the drill while inserted therein, and further while screw 10 is screwed into the bone at the rear wall of the drill. According to a preferred embodiment of the present invention, and as best seen in FIG. 2c, neck portion 30 is round in cross section, whereas grooves 32 interfere with its round contour or roundness by forming intrusions thereat.

According to a preferred embodiment of the present invention and as shown in FIG. 2a, surgical inserter 20 includes a handle 34 connected to, connectable to, or integrally formed with, neck portion 30. Handle 34 serves for pushing and rotating inserter 20, to thereby facilitate its insertion through the drill formed in the bone and its screwing into the bone at the rear wall of the drill. In a preferred embodiment handle 34 is connectable/removable from neck 30. To this end, handle 34 is formed with a threaded bore 36 for accepting a threaded screw 38 formed at the proximal end of neck portion 30. A screw 40 of handle 34 then serves to unrotationally secure neck portion 30 and handle 34 together.

FIGS. 3a–b illustrate a surgical sleeve according to the present invention, which is referred to hereinbelow as surgical sleeve 50. Surgical sleeve 50 serves for covering surgical inserter 20 and the band of connective tissue while inserting surgical screw 10 and the band of connective tissue through the drill formed in the bone, and screwing the surgical screw into the rear wall of the drill formed in the bone, to thereby fully protect the band of connective tissue during these procedures. Surgical sleeve 50 includes a hollow sleeve element 52 which is typically cylindrical and a base element 54 shaped and dimensioned to accommodate handle 34 of surgical inserter 20, to thereby prevent rotation of surgical sleeve 50 with respect to surgical inserter 20.

Surgical screw 10, surgical inserter 20 and surgical sleeve 50 are preferably made of a metal, e.g., stainless steel.

The operation of surgical screw 10, surgical inserter 20 and surgical sleeve 50 is as follows. A band of connective tissue is inserted through ring 16 of surgical screw 10, 50 as to have free ends of substantially equal length. Ring 16 is inserted into ring acceptor 24 of surgical inserter 20 and the free ends of the band of connective tissue, which hang out through openings 28 of head portion 22 of surgical inserter 20, are engaged within longitudinal grooves 32. Handle 34 is connected to neck portion 30 of surgical inserter 20. Then, surgical sleeve 50 is dressed over surgical inserter 20 and is rotationally stabilized by having base element 54 thereof engage handle 34. Sleeve element 52 of surgical sleeve 50 now protects the band of connective tissue from damages which may be imposed thereon while inserting the assembly through the drill formed in the bone and while screwing surgical screw 10 into the bone at the rear wall of the drill.

The surgical tools described herein in accordance with the present invention can be used for implementing a surgical method of anchoring a band of connective tissue to a rear wall of a drill formed in a bone. The method according to this aspect of the present invention is effected by implementing the following method steps in which, in a first step, a surgical screw having a ring is provided. In a second step, a band of connective tissue is inserted through the ring. Finally, a surgical inserter is used to insert the screw into the drill and further to screw the screw into the rear wall of the drill. According to a preferred embodiment, the method is further effected by covering the surgical inserter with a surgical sleeve, thereby protecting the band of connective tissue while inserting the screw into the drill and further while screwing the screw into the rear wall of the drill.

According to yet another aspect of the present invention there is provided a novel anterior cruciate ligament reconstruction surgical procedure for reconstructing a damaged anterior cruciate ligament of a knee joint. The procedure can be performed employing open knee surgery, however it is preferably performed using a minimal invasive procedure aided by knee arthroscopy as further detailed hereinunder.

Figure 5:
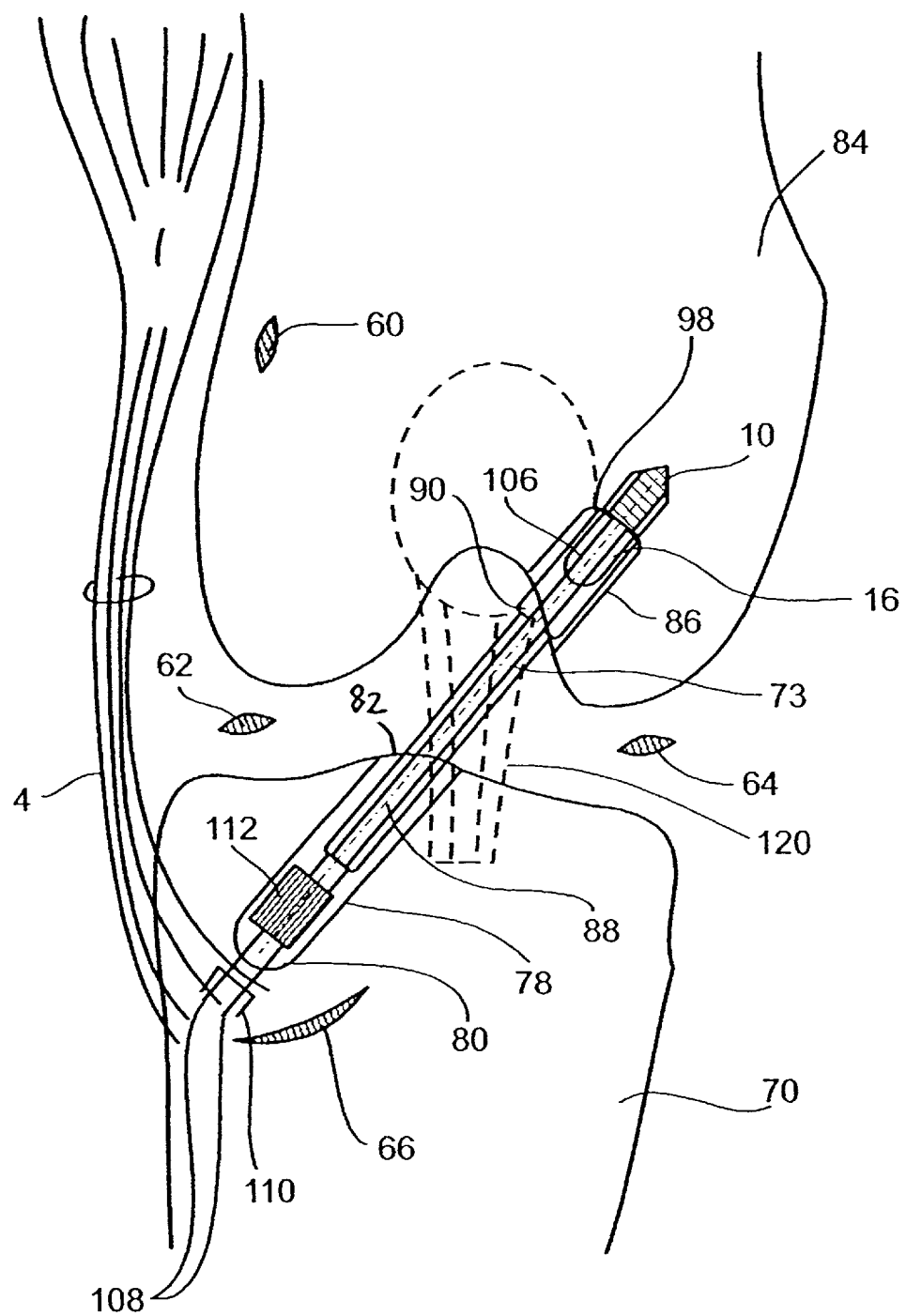
FIG. 5 is a schematic depiction of the results of a surgical method of anterior cruciate ligament reconstruction according to the present invention.

As shown in FIG. 5, superomedial 60, anteromedial 62 and anterolateral 64 portals, as well as a tibial incision 66 are formed in the knee of the patient. Portal 60 serves for inflow of saline; portal 64 serves for insertion of an arthroscope having illumination and suction channels; whereas portal 62 serves for insertion of surgical tools, as required. Different arrangements are also known and/or envisaged.

Tibial incision 66 serves for disconnecting a portion of the pes anserinus tendon 68 from the tibia 70, which portion is also disconnected from the thigh muscle 72 and is pulled out of the joint to serve as a band of connective tissue 73 to reconstruct the damaged anterior cruciate ligament of the knee joint. The portion of the pes anserinus tendon can include the semitendinosus 74 or the semitendinosus and the gracilis 76.

Tibial incision 66 further serves for drilling a first drill 73 in the tibia. Drill 78 has an entrance opening 80 and an exit opening 82 which faces the femur 84. Drilling drill 78 is preferably effected by a canulated drill, as well known in the art.

Then, a second drill 86 is formed in the femur. Drill 86 preferably co-aligns with drill 78 along the original path 88 of the damaged anterior cruciate ligament. Drill 86 has an entrance opening 90 and a rear wall 98 of femur bone.

Drilling drill 86 is preferably effected by a drilling device 100 as shown in FIG. 4. Drilling device 100 includes a drilling guide 102 and a drilling head 104. Drilling guide 102 is connectable to a rotating machine which rotates device 100 a selected number of revolutions per minute. Drilling guide 102 is selected wider than drilling head 104, therefore, the deepest drill that is drillable using drilling device 100 matches the length of drilling head 100. The length of drilling head 100 is therefore selected to match a desired depth for drill 86. In order to co-align drills 78 and 36, while drilling drill 86, drilling device 100 is inserted through drill 78, such that guide 102 is at least in part supported by the side walls of drill 78 to thereby ensure co-alignment as described.

At this stage, the band of connective tissue 73 is inserted through ring 16 of surgical screw 10, 50 as to have free ends of substantially equal length. Ring 16 is inserted into ring acceptor 24 of surgical inserter 20 and the free ends of the band of connective tissue 73, which hang out through openings 28 of head portion 22 of surgical inserter 20, are engaged within longitudinal grooves 32 (FIG. 2a). Handle 34 is connected to neck portion 30 of surgical inserter 20 (FIG. 2a). Then, surgical sleeve 20 is dressed over surgical inserter 20 and is rotationally stabilized by having base element 54 (FIG. 3a–b) thereof engage handle 34.

This assembly is now inserted, screw 10 first, through entrance opening 80 of drill 78 into drill 86, and screw 10 is thereafter screwed into the tibial bone at rear wall 98 of drill 86. Then, inserter 20 as well as sleeve 50 are retracted from the knee joint, leaving the band of connective tissue 73 anchored to the tibia via screw 10 through the folded end 106 thereof and the free ends 108 thereof protruding out of entrance opening 80 of drill 78.

The free ends 108 of the band of connective tissue 73 are attached to the tibia 70 either via surgical staple(s) 110, or alternatively via an interference screw 112 inserted into drill 78, biasing ends 73 against the side wall thereof.

In a case wherein ring 16 is connectable to screw head 12, screw head 12 can first be screwed into the femur by conventional means, whereas only ring 16 is engaged with inserter 20 and sleeve 50 to thereby insert ring 16 and the band of connective tissue 73 as described, and attach, e.g., by a snapping mechanism, the ring to the pre-screwed screw head 12.

The band of connective tissue according to the present invention can be a band of an artificial connective tissue. Preferably, the band of connective tissue is a band of a ligament, a tendon or a portion thereof, most preferably, the band of connective tissue is derived from a pes anserinus tendon.

The present invention enjoy numerous advantages. First, since the drill formed in the femur is dead end, the chances of developing post operation infections are reduced as compared with a procedure in which both the tibial and the femoral drills have two open ends. Second, since the band of connective tissue is not derived from the patella tendon (marked at 120 in FIG. 5), complications associated with fractured patella or damaged patella tendon are not experienced. And last but not least, immediate post operation full weight bearing is enabled by the surgical procedure of the present invention.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A surgical inserter for inserting through a drill formed in a bone and for screwing into a rear wall of the drill formed in the bone a surgical screw having a ring, through which ring a band of connective tissue being inserted, the surgical inserter comprising:
   (a) a head portion being formed with a ring acceptor for accepting the ring of the surgical screw; and
   (b) a neck portion being connected to, or integrally formed with, said head portion, said neck portion being formed with two longitudinal grooves extending from said head portion to a proximal end of said neck portion, said two longitudinal grooves being for accepting and protecting the band of connective tissue therein, so as to enable inserting the surgical screw and the band of connective tissue through the drill formed in the bone, and screwing the surgical screw into the rear wall of the drill formed in the bone with minimized damage to the band of connective tissue.

2. The surgical inserter of claim 1, further comprising a handle connected to, or integrally formed with, said neck portion at said proximal end.

3. The surgical inserter of claim 2, wherein said handle is removable.

4. The surgical inserter of claim 1, wherein said ring acceptor is U-shaped.

5. The surgical inserter of claim 1, wherein said ring acceptor includes undercuts formed in said head portion.

6. The surgical inserter of claim 1, wherein said neck is round in cross section, whereas said two longitudinal grooves interfere with said roundness.

7. A set of surgical tools comprising:
   (a) a surgical inserter for inserting through a drill formed in a bone and for screwing into a rear wall of the drill formed in the bone a surgical screw having a ring, through which ring a band of connective tissue being inserted, the surgical inserter including:
      (i) a head portion being formed with a ring acceptor for accepting the ring of the surgical screw; and
      (ii) a neck portion being connected to, or integrally formed with, said head portion, said neck portion being formed with two longitudinal grooves extending from said head portion to a proximal end of said neck portion, said two longitudinal grooves being for accepting and protecting the band of connective tissue therein, so as to enable inserting the surgical screw and the band of connective tissue through the drill formed in the bone, and screwing the surgical screw into the rear wall of the drill formed in the bone with minimized damage to the band of connective tissue; and
   (b) a surgical sleeve for covering said inserter and the band of connective tissue while inserting the surgical screw and the band of connective tissue through the drill formed in the bone, and screwing the surgical screw into the rear wall of the drill formed in the bone.

8. The set of surgical tools of claim 7, wherein said surgical inserter further includes a handle connected to, or integrally formed with, said neck portion at said proximal end.

9. The set of surgical tools of claim 8, wherein said handle is removable.

10. The set of surgical tools of claim 7, wherein said ring acceptor is U-shaped.

11. The set of surgical tools of claim 7, wherein said ring acceptor includes undercuts formed in said head portion.

12. The set of surgical tools of claim 7, wherein said neck is round in cross section, whereas said two longitudinal grooves interfere with said roundness.

* * * * *